United States Patent [19]

Barton et al.

[11] 4,203,925
[45] May 20, 1980

[54] PROCESS FOR THE PRODUCTION OF SPIRODIENONES AND SPIROCYCLIC KETONES

[75] Inventors: Derek H. R. Barton, Gif-sur-Yvette, France; Brian J. Willis, Bergenfield, N.J.

[73] Assignee: Fritzsche Dodge & Olcott Inc., New York, N.Y.

[21] Appl. No.: 914,160

[22] Filed: Jun. 9, 1978

[51] Int. Cl.$^2$ ............................................. C07C 45/00
[52] U.S. Cl. ................................ 568/362; 252/522 R; 260/456 R; 260/456 P; 260/586 P; 568/377; 568/774
[58] Field of Search ........... 260/586 P, 586 G, 586 C, 260/456 R, 456 P; 568/774

[56] References Cited

FOREIGN PATENT DOCUMENTS 2353147  5/1974  Fed. Rep. of Germany ...... 260/586 G

OTHER PUBLICATIONS

Bozzato et al., "CA", 84:90326x (1976).
Stork et al., "CA", 78:31559z (1973).
Caine et al., "CA", 81:37663s (1974).
Marshall et al., "CA", 69:27539a (1968).
Marshall et al., "CA", 72:43903a (1970).
McCurry et al., "79" 18873c (1973).
Coxon et al., "82" 73206z (1975).
Hikino et al., "Tetra", vol. 27, pp. 4831-4836 (1971).

*Primary Examiner*—Norman Morgenstern
*Attorney, Agent, or Firm*—Cooper, Dunham, Clark, Griffin & Moran

[57] ABSTRACT

This invention concerns processes for preparing compounds having the structure

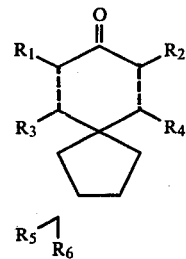

wherein each of $R_1$, $R_2$, $R_3$, $R_4$, $R_5$ and $R_6$ is the same or different and represents hydrogen or a lower alkyl group and wherein each dashed line represents a carbon-carbon single bond or a carbon-carbon double bond. Those compounds in which all three dashed lines represent carbon-carbon double bonds are prepared by reacting phenols and 2-alkylidene-1,4-disubstituted butanes. Selective reduction of these compounds yields those in which at least one dashed line represents a carbon-carbon single bond. Most of the compounds so prepared are new compounds. All are useful as fragrance materials either directly and/or in compositions and/or have useful fixative properties in fragrance compositions.

9 Claims, No Drawings

PROCESS FOR THE PRODUCTION OF SPIRODIENONES AND SPIROCYCLIC KETONES

BACKGROUND OF THE INVENTION

Materials which provide woody fragrance notes and/or exhibit fixative properties when included in fragrance compositions are well-known in the art of perfumery. Natural materials, for example, the essential oils derived from sandalwood, patchouli and vetiver plant species are used extensively in the perfume and cosmetic industries. These oils would find even greater use if it were not for their limited supply and high cost. Accordingly, there is a continued effort on the part of research chemists and perfumers to find synthetic materials which can effectively replace those fragrance notes and fixative effects provided by natural oils.

SUMMARY OF THE INVENTION

The present invention provides processes for preparing compounds having the structure:

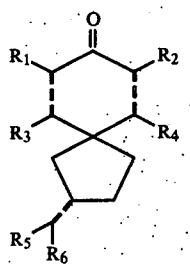
I wherein each of $R_1$, $R_2$, $R_3$, $R_4$, $R_5$, and $R_6$ is the same or different and represents hydrogen or a lower alkyl group and wherein each dashed line represents a carbon-carbon single bond or a carbon-carbon double bond.

One process of the invention involves reacting a phenol having the structure:

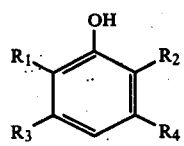
II and a 2-alkylidene-1,4-disubstituted butane having the structure:

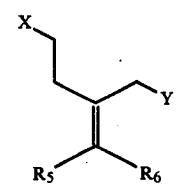
III wherein X and Y are selected from the group consisting of halogens and sulfonate groups of the structure $-O-SO_2-R$ where R may be an aliphatic or aromatic hydrocarbon moiety, or wherein X and Y together form a cyclic sulfate group of the structure

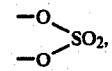

at a temperature in the range from about $-70°$ to $+140°$ C. and in the presence of a base, to form an intermediate having the structure:

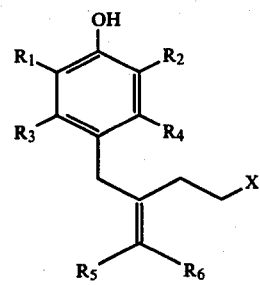
IV

This intermediate is isolated and converted in the presence of a base and at a temperature in the range from about $-70°$ to $+220°$ C. to a spirodienone compound having the structure:

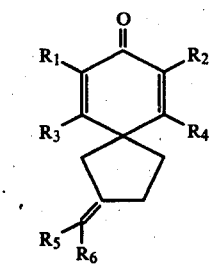
V

Alternatively, the reaction of phenol II and 2-alkylidene-1,4-disubstituted butane III in the presence of a base and at a temperature in the range from about $-70°$ to $+220°$ C. can provide spirodienone V directly. Longer reaction times, higher reaction temperatures and stronger bases favor direct conversion of the intermediate IV to spirodienone V, thereby avoiding isolation of the intermediate IV.

The invention also provides a process of preparing spirocyclic ketone compounds having the structure I provided that at least one dashed line represents a carbon-carbon single bond. This process involves the selective reduction of spirodienone V to spirocyclic ketone I wherein one, two, or all three carbon-carbon double bonds are reduced to carbon-carbon single bonds.

The invention further provides novel spirodienone and spirocyclic ketone compounds useful as fragrance materials.

Finally, the invention provides fragrance compositions which contain the spirodienone and/or spirocyclic ketone compounds in amounts effective to impart fragrance thereto.

How these and other objects of the invention are accomplished will be better understood upon reading the detailed description and claims which follow. In at least one embodiment of the invention at least one of the foregoing objects is achieved.

DETAILED DESCRIPTION OF THE INVENTION

In particular, the invention provides a process for the preparation of substituted spirodienone compounds having the structure:

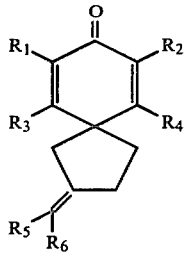

V wherein each of $R_1$, $R_2$, $R_3$, $R_4$, $R_5$ and $R_6$ is either the same or different and represents either hydrogen or a lower alkyl group, that is, an alkyl group having one to three carbon atoms. All such compounds are novel except the spirodienone wherein simultaneously $R_1=R_2=H$ and $R_3=R_4=R_5=R_6=-CH_3$. This compound is known but has not previously been prepared by the process described herein.

These spirodienones are readily reduced to spirocyclic ketone compounds having the structure:

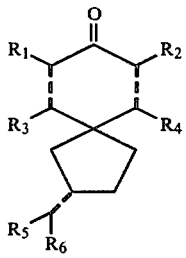

I wherein $R_1$, $R_2$, $R_3$, $R_4$, $R_5$ and $R_6$ are as described hereinabove and wherein each dashed line represents either a carbon-carbon single bond or a carbon-carbon double bond provided that at least one dashed line represents a carbon-carbon single bond.

All such spirocyclic ketones are new except those wherein simultaneously $R_1=R_2=H$ and $R_3=R_4=R_5=R_6=-CH_3$. These compounds are known but have not previously been prepared by the process described herein.

Compounds V are prepared by reacting phenols having the structure:

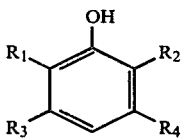

II wherein $R_1$, $R_2$, $R_3$ and $R_4$ are as described previously with 2-alkylidene-1,4-disubstituted butanes having the structure:

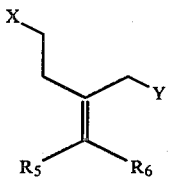

III wherein X and Y are selected from the group consisting of halogens such as bromine, chlorine, or iodine, preferably chlorine or bromine, and sulfonate groups of the structure $-O-SO_2-R$ where R may be an aliphatic or aromatic hydrocarbon moiety, such as methyl or para-tolyl. Alternatively, X and Y together may form a cyclic sulfate group of the structure

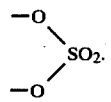

$R_5$ and $R_6$ are as described previously. When X and Y are either halogens or sulfonate groups it is usually convenient that $X=Y$.

Specific examples of phenols (II) falling within the scope of the foregoing structural formula include the following:
3,5-dimethylphenol
3,5-diethylphenol
3,5-dipropylphenol
2,3,5-trimethylphenol
2,3,5-triethylphenol
2,3,5-tripropylphenol
2,3,5,6-tetramethylphenol
2,3,5,6-tetraethylphenol
2,3,5,6-tetrapropylphenol
2,6-diethyl-3,5-dimethylphenol
2,6-dipropyl-3,5-dimethylphenol
2,6-dimethyl-3,5-diethylphenol
2,6-dimethyl-3,5-dipropylphenol
2,3-dimethyl-5,6-diethylphenol
2,3-dimethyl-5,6-dipropylphenol
2,3-diethyl-5,6-dipropylphenol
2,5-dimethyl-3,6-diethylphenol
2,5-dimethyl-3,6-dipropylphenol
2,5-diethyl-3,6-dipropylphenol Specific examples of 2-akylidene-1,4-disubstituted butanes (III) falling within the scope of the foregoing formula are 2-(2'-propylidene)-1,4-dichlorobutane, 2-(2'-butylidene)-1,4-dibromobutane, 2-(2'-pentylidene)-1,4-bis (para-toluene sulfonyl) butane and

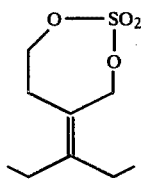

The alkylation is effected by reacting compounds II and III at a temperature in the range from about $-70°$ to $+140°$ C., preferably in the range from about $-30°$ to $+110°$ C., in the presence of a base. Shorter reaction times, lower reaction temperatures, and weaker bases favor formation of an intermediate having the structure:

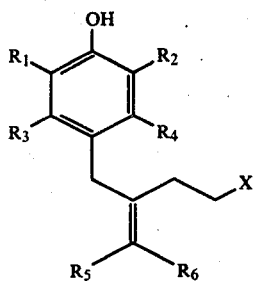

which may be isolated by standard procedures. The intermediate IV is then converted in the presence of a base, either the same as or different from the base present during alkylation, and at a temperature in the range from about −70° to +220° C., preferably in the range from about −30° to +220° C., to a spirodienone compound having the structure:

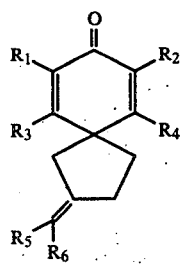

wherein $R_1$, $R_2$, $R_3$, $R_4$, $R_5$ and $R_6$ are as described previously.

If the spirodienone V is volatile, the spiroannulation is conveniently carried out in a high boiling solvent, or in the absence of a solvent, at a temperature in the range from about +140° to +220° C. under vacuum, such that compound V distills from the reaction vessel as it is formed. Alternatively, the product (V) is isolated and purified by conventional techniques.

It is also possible to accomplish both the alkylation and spiroannulation steps without isolation of intermediate IV. Compounds II and III are reacted at a temperature in the range from about −70° to +220° C. in the presence of a base. Longer reaction times, higher reaction temperatures, and stronger bases favor formation of the spirodienone V directly.

As in the case where intermediate IV is isolated and converted to spirodienone V, the reaction may be carried out in a high boiling solvent, or in the absence of solvent, if the spirodienone is volatile. Compound V may then be vacuum distilled from the reaction vessel at the end of the reaction. Alternatively, the product V may be isolated and purified by conventional techniques.

A wide variety of bases are useful for this reaction including: alkali metal hydroxides, such as sodium hydroxide and potassium hydroxide, as well as alkaline earth metal hydroxides, such as calcium hydroxide and barium hydroxide; alkali metal and alkali earth metal salts, such as carbonates, acetates, borates, e.g. sodium carbonate and sodium acetate; alkali metal and alkali earth metal alkoxides, such as potassium t-butoxide, sodium ethoxide and magnesium methoxide; metal hydrides, such as sodium hydride; organic bases, including primary, secondary and tertiary amines such as mono- methylamine, diethylamine and tributylamine, polyamines, such as ethylene diamine, heterocyclic amines, such as morpholine and pyridine, and alkylolamines, such as diethanolamine. Ammonia and inorganic ammonium salts that hydrolyze to form ammonia in the presence of metal hydroxides, such as ammonium chloride are effective. Also, ion exchange resins are effective.

These reactions may be carried out in aqueous or non-aqueous solvent systems, or in the absence of a solvent. Thus, useful solvent systems include water, ethyl alcohol, dimethylformamide, tetrahydrofuran, hexane, toluene, tetralin, mineral oil, dibutylphthalate, and mixed solvent systems such as water/ethyl alcohol, water/tetrahydrofuran, and toluene/dimethylformamide.

Further, these reactions may advantageously be catalyzed by metal salts such as copper sulfate, copper chloride, copper oxide, ferrous sulfate, cobalt chloride and by phase-transfer catalysts such as benzyl triethylammonium chloride.

The spirodienone compounds V are converted to spirocyclic ketone compounds I by reduction using any of a number of conventional techniques including metal catalyzed, e.g. palladium, platinum, and/or nickel catalyzed, hydrogenation or metal/ammonia or metal/amine reduction.

Thus, selective reduction of spirodienones having the structure:

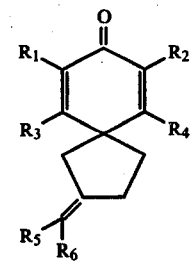

yields spirocyclic ketone compounds, including isomers, having the following structures:

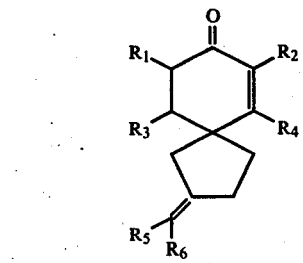

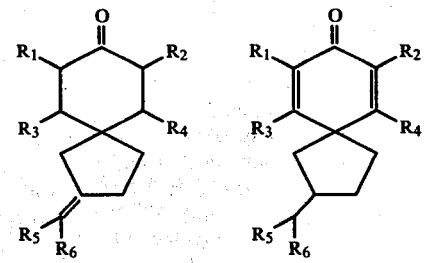

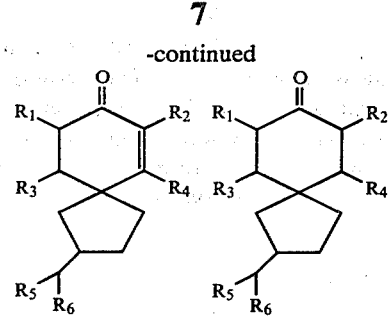

-continued

Isolation and purification of the final products is achieved by conventional techniques including extraction, distillation, crystallization, preparative chromatographic techniques, and the like.

Compounds I of the invention exhibit warm woody earthy notes rendering them useful as fragrance materials. They also exhibit such notes and/or have useful fixative effects when incorporated into fragrances and fragrance compositions in amounts effective to impart fragrance thereto, such as amounts in the range from about 0.01%–80% by weight thereof.

One specific example of a compound prepared according to the process of this invention is represented by structure VI.

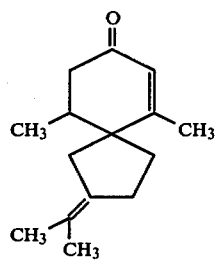

This structure represents epimeric compounds, one of which is commonly referred to as β-vetivone, a known component of the oil obtained by steam distillation of the roots of *Vetiveria zizanioides*, and generally considered to be an important contributor to the overall odor character of the oil.

Another compound, 2-isopropylidene-7,9-dimethyl-spiro [4.5] decan-8-one, prepared according to the process of this invention has the structure:

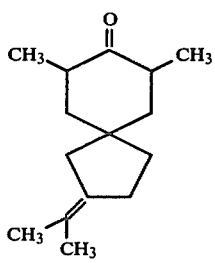

This spirocyclic ketone, saturated in the six-membered ring, unexpectedly has been found to have particularly desirable fragrance and fixative properties.

Additionally, the compounds 2-n-propyl-7,9-dimethyl-spiro [4.5] decan-8-one, 2-isobutylidene-6,10-dimethyl-spiro [4.5] dec-6-en-8-one, and 2-isopropylidene-7,9-dimethyl-spiro [4.5] dec-6-en-8-one have particularly desirable fragrance and fixative properties.

The following examples are set forth to more fully illustrate the practices of this invention, but are in no way meant to limit the scope thereof. Percentages set forth are by weight unless otherwise indicated.

EXAMPLE 1

To a solution of 3,5-dimethylphenol (6.71 g.) in ethyl alcohol (10.0 ml.) was added a solution of $CuCl_2.2H_2O$ (1.0 g.) in water (100 ml.). 58% aqueous ammonia (10.0 ml.) was added, followed by 2-isopropylidene-1,4-dichlorobutane (12.0 g.). After 24 hours the reaction mixture was quenched with cold dilute mineral acid and the organic material extracted with chloroform. Workup provided 3,5-dimethylphenol (2.7 g.) and alkylation product (6.3 g.).

The crude alkylation product was mixed with one equivalent of powdered sodium hydroxide and the mixture heated at 140°–160° C. under vacuum. The distillate was chromatographed on silica gel to provide the desired spirodienone (V, $R_1=R_2=H$, $R_3=R_4=R_5=R_6=CH_3$) in 30% yield. The identity of the compound was verified by IR and NMR based upon the following data: $\nu$ max 1660, 1620, 1260, 915, 740 $cm^{-1}$, $\delta(CDCl_3)$ 6.0 (2H,s), 2.4 (6H,m), 1.95 (6H,s), 1.65 (6H,d) $\mu$ max (EtOH) 246 nm.

EXAMPLE 2

Spirodienone from Example 1 (0.21 g.), 5% palladium on carbon (0.02 g.) and ethyl alcohol (100 ml.) were shaken under an atmosphere of hydrogen. The hydrogenation was interrupted when one equivalent of gas had been taken up. The solution was filtered, solvent evaporated, and the product chromatographed on silica gel to provide a mixture of β- and epi β-vetivone (VI) (7:3 ratio) in 51% yield.

EXAMPLE 3

Spirodienone V, wherein $R_1=R_2=R_5=R_6=CH_3$ and $R_3=R_4=H$ (0.2 g.), 5% palladium on carbon (0.02 g.) and ethyl alcohol (100 ml.) were shaken under an atmosphere of hydrogen. The hydrogenation was interrupted when two equivalents of gas had been taken up. The solution was filtered, and the solvent evaporated to provide (as a mixture of isomers) 2-isopropylidene-7,9-dimethyl-spiro [4.5] decan-8-one in essentially quantitative yield. The product exhibited the expected spectral properties.

EXAMPLE 4

An oil vetiver substitute may be prepared. This composition contains the following:

| | |
|---|---|
| 50% | 2-Isopropylidene-7,9-dimethyl-spiro [4.5] decan-8-one |
| 15 | Oil Cedarwood |
| 10 | Vetiver Acetate |
| 10 | Cedryl Acetate |
| 1 | Iso Eugenol |
| 4 | Terpineol |
| 5 | Durofix |
| 5 | Geranyl Acetate |
| 100% | |

EXAMPLE 5

Another oil vetiver substitute may be prepared containing the following:

| | |
|---|---|
| 1% | Oil Patchouly |
| 1 | Geraniol from Palmarosa |
| 3 | Ionone Residue |
| 12 | Oil Copaiba |
| 13 | Cedryl Acetate |
| 16 | Oil Guaiacwood |
| 15 | Oil Cedarwood |
| 5 | Terpineol |
| 9 | Oil Bois De Rose |
| 25 | 2-Isopropylidene-7,9-dimethyl-spiro [4.5] decan-8-one |
| 100% | |

EXAMPLE 6

A lavender fragrance composition may be prepared which contains:

| | |
|---|---|
| 1% | Oakmoss Absolute |
| 5 | 2-n-Propyl-7,9-dimethyl-spiro [4.5] decan-8-one |
| 4 | Musk Xylene |
| 5 | Oil Rosemary |
| 3 | Oil Petitgrain Paraguay |
| 5 | Benzyl Acetate |
| 7 | Oil Bois De Rose |
| 10 | Coumarin |
| 10 | Terpinyl Acetate |
| 20 | Oil Spike Lavender |
| 30 | Oil Lavandin |
| 100% | |

EXAMPLE 7

A chypre fragrance composition may be prepared which contains the following:

| | |
|---|---|
| 0.5% | Oil Angelica Root |
| 0.5 | Castoreum Absolute |
| 1.0 | Oil Rose |
| 1.0 | Civet Absolute |
| 1.0 | Oakmoss Absolute |
| 2.0 | 2-Isopropylidene-7,9-dimethyl-spiro [4.5] decan-8-one |
| 2.0 | Musk Ambrette |
| 3.0 | Resinoid Labdanum |
| 5.0 | Oil Ylang Ylang |
| 6.0 | Benzyl Acetate |
| 7.0 | Oil Sandalwood |
| 6.0 | Vanillin |
| 9.0 | Benzyl Alcohol |
| 12.0 | Jasmine Extract |
| 12.0 | Coumarin |
| 12.0 | Phenyl Ethyl Alcohol |
| 20.0 | Oil Bergamot |
| 100.0% | |

EXAMPLE 8

A santal fragrance may be prepared which contains:

| | |
|---|---|
| 10% | Terpineol |
| 20 | Oil Cedarwood |
| 5 | Oil Cassia |
| 10 | Coumarin |
| 5 | Musk Xylene |
| 30 | Oil Sandalwood |
| 15 | 2-n-propyl-7,9-dimethyl-spiro [4.5] decan-8-one |
| 5 | Resinoid Styrax |
| 100% | |

EXAMPLE 9

A Jasmin fragrance may be prepared which contains:

| | |
|---|---|
| 0.1% | 2-Isopropylidene-7,9-dimethyl-spiro [4.5] dec-6-en-8-one |
| 0.5 | Gamma Undecalactone |
| 0.5 | Para Cresyl Phenylacetate |
| 0.9 | Ethyl Cinnamate |
| 7.0 | Oil Ylang Ylang |
| 6.0 | Geranyl Acetate |
| 5.0 | Alpha Amyl Cinnamic Aldehyde |
| 10.0 | Linalool Synthetic |
| 20.0 | Benzyl Acetate |
| 20.0 | Phenylethyl Alcohol |
| 30.0 | Hydroxy Citronellal |
| 100.0% | |

EXAMPLE 10

A violet fragrance may be prepared containing the following:

| | |
|---|---|
| 0.6% | Musk Ambrette |
| 0.3 | Jasmin Absolute |
| 0.1 | Violet Leaves Absolute |
| 1.0 | Heliotropin |
| 3.0 | Methyl Ionone |
| 2.0 | Benzoin Siam |
| 3.0 | 2-Isopropylidene-7,9-dimethyl-spiro [4.5] dec-6-en-8-one |
| 20.0 | Oil Cedarwood |
| 30.0 | Oil Sandalwood |
| 40.0 | Oil Orris Root |
| 100.0% | |

EXAMPLE 11

A fougere fragrance may be prepared containing the following:

| | |
|---|---|
| 0.2% | Undecylenic Aldehyde |
| 0.3 | Civet Absolute |
| 0.5 | Vanillin |
| 0.5 | Rose Otto |
| 0.5 | Acetophenone |
| 1.0 | Anisic Aldehyde |
| 1.0 | Oil Clary Sage |
| 2.0 | Iso Amyl Salicylate |
| 2.0 | Oil Patchouly |
| 3.0 | Jasmin Absolute |
| 3.0 | Oil Sandalwood |
| 4.0 | Linalool Synthetic |
| 5.0 | 2-Isobutylidene-7,9-dimethyl-spiro [4.5] decan-8-one |
| 7.0 | Coumarin |
| 10.0 | Benzyl Acetate |
| 10.0 | Oil Bois De Rose |
| 20.0 | Oil Lavender |
| 30.0 | Oil Bergamot Rectified |
| 100.0% | |

As will be obvious to one skilled in the art, many modifications, variations and alterations are possible in the practices of this invention without departing from the spirit and scope thereof.

We claim:

1. A process for preparing a spirodienone compound having the structure:

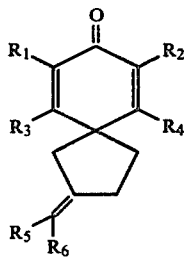

wherein each of $R_1$, $R_2$, $R_3$, $R_4$, $R_5$ and $R_6$ is the same or different and represents hydrogen or a lower alkyl group which comprises reacting a phenol having the structure:

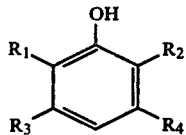

and a 2-alkylidene-1,4-disubstituted butane having the structure:

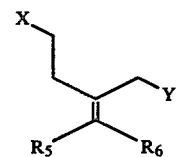

wherein X and Y are selected from the group consisting of halogens and sulfonate groups of the structure —O—SO$_2$—R where R may be an aliphatic or aromatic hydrocarbon moiety, or wherein X and Y together form a cyclic sulfate group of the structure

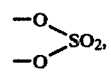

in the presence of a base and at a temperature in the range from about −70° to +220° C. to form said spirodienone compound.

2. A process for preparing a spirodienone compound having the structure:

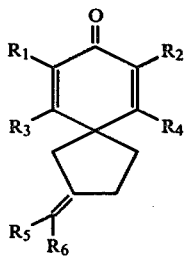

wherein each of $R_1$, $R_2$, $R_3$, $R_4$, $R_5$ and $R_6$ is the same or different and represents hydrogen or a lower alkyl group which comprises reacting a phenol having the structure:

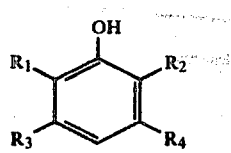

and a 2-alkylidene-1,4-disubstituted butane having the structure:

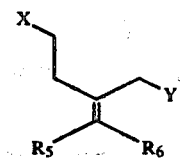

wherein X and Y are selected from the group consisting of halogens and sulfonate groups of the structure —O—SO$_2$—R where R may be an aliphatic or aromatic hydrocarbon moiety, or wherein X and Y together form a cyclic sulfate group of the structure

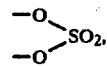

at a temperature in the range from about −70° to +140° C. and in the presence of a base to form an intermediate having the structure:

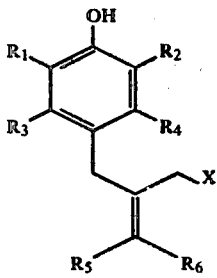

isolating and converting said intermediate in the presence of a base and at a temperature in the range from about −70° to +220° C. to said spirodienone compound.

3. The process of claim 2 wherein $R_1=R_2=H$ and $R_3=R_4=R_5=R_6=$—$CH_3$.

4. The process of claim 3 wherein said first base is ammonium hydroxide, said phenol is 3,5-dimethylphenol, said 2-alkylidene-1,4-disubstituted compound is 2-isopropylidene-1,4-dichlorobutane, and said second base is an alkali metal hydroxide.

5. A process for preparing a spirocyclic ketone compound having the structure:

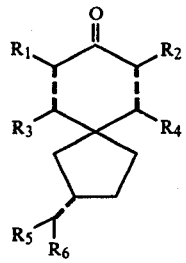

wherein each of $R_1$, $R_2$, $R_3$, $R_4$, $R_5$ and $R_6$ is the same or different and represents hydrogen or a lower alkyl group and wherein each dashed line represents a carbon-carbon single bond or a carbon-carbon double bond provided that at least one dashed line represents a carbon-carbon single bond which comprises reacting a phenol having the structure:

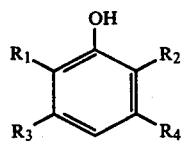

and a 2-alkylidene-1,4-disubstituted butane having the structure:

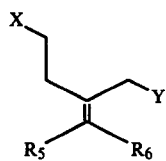

wherein X and Y are selected from the group consisting of halogens and sulfonate groups of the structure $-O-SO_2-R$ where R may be an aliphatic or aromatic hydrocarbon moiety, or wherein X and Y together form a cyclic sulfate group of the structure

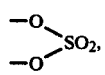

at a temperature in the range from about $-70°$ to $+140°$ C. and in the presence of a base to form an intermediate having the structure:

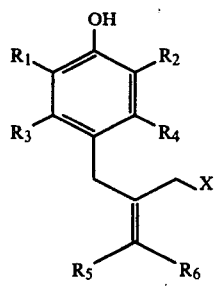

isolating and converting said intermediate in the presence of a base and at a temperature from about $-70°$ to $+220°$ C. to a spirodienone compound having the structure:

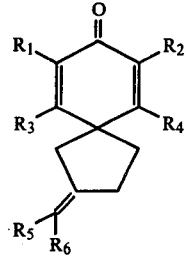

and reducing the spirodienone compound to produce said spirocyclic ketone compound.

6. The process of claim 5 wherein $R_1=R_2=H$ and $R_3=R_4=R_5=R_6=-CH_3$.

7. The process of claim 6 wherein said reduction comprises hydrogenating said spirodienone compound with hydrogen gas in the presence of a hydrogenation catalyst.

8. A process for preparing a spirocyclic ketone compound having the structure:

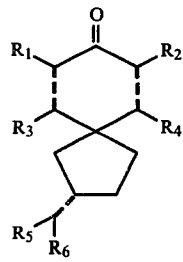

wherein each of $R_1$, $R_2$, $R_3$, $R_4$, $R_5$, and $R_6$ is the same or different and represents hydrogen or a lower alkyl group and wherein each dashed line represents a carbon-carbon single bond or a carbon-carbon double bond provided that at least one dashed line represents a carbon-carbon single bond which comprises reducing the compound of claim 1.

9. A process of preparing a spirocyclic ketone in accordance with claim 5 wherein $R_1$ and $R_2$ represent hydrogen and wherein $R_3$, $R_4$, $R_5$ and $R_6$ represent a methyl group and wherein one of the dashed lines in the 6-membered carbon ring represents a carbon-carbon double bond and the other dashed line represents a carbon-carbon single bond, and wherein the dashed line from the 5-membered carbon ring is a carbon-carbon double bond, such spirocyclic ketone having the structural formula:

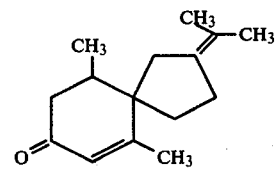

* * * * *

UNITED STATES PATENT AND TRADEMARK OFFICE
CERTIFICATE OF CORRECTION

Page 1 of 2

PATENT NO. : 4,203,925
DATED : May 20, 1980
INVENTOR(S) : Derek H. R. Barton and Brian J. Willis It is certified that error appears in the above-identified patent and that said Letters Patent are hereby corrected as shown below:

In the Abstract change the structure from

" 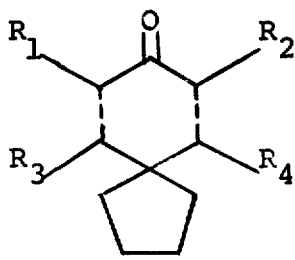 "

to

-- 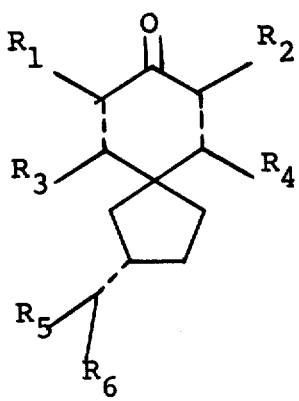 --

UNITED STATES PATENT AND TRADEMARK OFFICE
CERTIFICATE OF CORRECTION

PATENT NO. : 4,203,925
DATED : May 20, 1980
INVENTOR(S) : Derek H. R. Barton and Brian J. Willis It is certified that error appears in the above-identified patent and that said Letters Patent are hereby corrected as shown below:

In Column No. 8, line 26, change "$\mu$ max" to --$\lambda$ max--.

In Column 9, Example 8, line 66 should be changed from "100%" to $-- \frac{\phantom{100\%}}{100\%} --$.

In Column 10, Example 11, line 59 should be changed from "100%" to $-- \frac{\phantom{100\%}}{100\%} --$.

Signed and Sealed this

Twelfth Day of August 1980

[SEAL]

Attest:

SIDNEY A. DIAMOND

Attesting Officer

Commissioner of Patents and Trademarks